United States Patent
Nesvadba et al.

(10) Patent No.: US 6,455,706 B2
(45) Date of Patent: Sep. 24, 2002

(54) POLYMERIZABLE COMPOSITIONS CONTAINING ALKOXYAMINE COMPOUNDS DERIVED FROM NITROSO- OR NITRONE COMPOUNDS

(75) Inventors: Peter Nesvadba, Marly; Andreas Kramer, Düdingen; Alfred Steinmann, Praroman; Werner Stauffer, Fribourg, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/829,479

(22) Filed: Apr. 9, 2001

Related U.S. Application Data

(62) Division of application No. 09/114,621, filed on Jul. 13, 1998, now Pat. No. 6,262,206.

(30) Foreign Application Priority Data

Jul. 15, 1997 (EP) ............................................. 97810487
Jul. 15, 1997 (EP) ............................................. 97810488

(51) Int. Cl.⁷ ........................................... C07D 207/46
(52) U.S. Cl. ...................... 548/542; 564/301; 558/303
(58) Field of Search .......................... 548/542; 564/300, 564/301; 558/303

(56) References Cited

U.S. PATENT DOCUMENTS

| 4,581,429 A | 4/1986 | Solomon et al. ............ 526/220 |
| 5,322,912 A | 6/1994 | Georges ..................... 526/204 |

FOREIGN PATENT DOCUMENTS

| BE | 619146 | 12/1962 |
| EP | 0135280 | 3/1985 |
| EP | 0735052 | 10/1996 |
| WO | 98/13392 | 4/1998 |

OTHER PUBLICATIONS

CA:104:224458 abs of Anal. Lett by Janzen et al 18(A14) pp 1749–57 1985.*
CA:131:45141 abs of Am. Chem. Soc by Benoit et al 121 (16) pp 3904–3920 1999.*
CA:133:238503 abs of WO 2000053640 Sep. 2000.*
CA:102:221335 abs of EP 135280 Mar. 1985.*
CA:128:68433 abs of JP09288339 Nov. 1997.*
CA:116:150914 abs of J. Chem. Soc., Chem. Commun. by Bunse et al (1) pp 47–9 1992.*
CA:116:175374 abs of Polym. Degrad. Stabl by Faucitano et al 35(3) pp 211–17 1991.*
Chem. Abstr. vol. 54, No. 14, p. 14163h, (1960).

Gingras et al., *Properties and Reactions of Free Alkyl Radicals in Solution* . Part VII, *Reactions with Quinone Imides, Nitric, Oxide, and Nitroso–compounds.*, (1954), pp. 1920–1924.
Michiko Iwamura et al., Bulletin of the Chemical Society of Japan, vol. 43, pp. 856–860, (1970).
J. Am. Chem. Soc. vol. 118, (1996), pp. 905–906.
Chem. Abstract 8593, (1963) for BE 619,146.

* cited by examiner

Primary Examiner—Jean F. Vollano
(74) Attorney, Agent, or Firm—Tyler A. Stevenson

(57) ABSTRACT

A polymerizable composition, comprising
a) at least one ethylenically unsaturated monomer or oligomer, and
b) an initiator compound of formula (I)

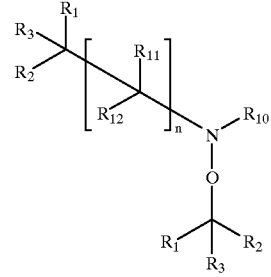

wherein n is 0 or 1.

The compounds of formula (I) are prepared from a free radical

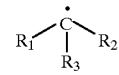

and a compound of formula $R_{10}NO$ or

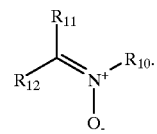

Further aspects of the present invention are a process for polymerizing ethylenically unsaturated monomers, novel initiator compounds and their use for polymerization, intermediate compounds and also the polymer or copolymer produced by this process.

4 Claims, No Drawings

POLYMERIZABLE COMPOSITIONS CONTAINING ALKOXYAMINE COMPOUNDS DERIVED FROM NITROSO- OR NITRONE COMPOUNDS

This application is a divisional of application Ser. No. 09/114,621, filed Jul. 13, 1998 now U.S. Pat. No. 6,262,206.

The present invention relates to a polymerizable composition comprising a) at least one ethylenically unsaturated monomer and b) a nitroxide initiator compound. Further aspects of the present invention are a process for polymerizing ethylenically unsaturated monomers, novel initiator compounds and their use for polymerization, and also the polymer or copolymer produced by this process.

More specifically, in one of its aspects the present invention relates to polymerizable compositions and polymerization processes which provide polymeric resin products having low polydispersity, which polymerization processes proceed with enhanced monomer to polymer conversion efficiencies. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

Polymers or copolymers prepared by free radical polymerization processes inherently have broad molecular weight distributions or polydispersities which are generally higher than about four. One reason for this is that most of the free radical initiators have half lives that are relatively long, ranging from several minutes to many hours, and thus the polymeric chains are not all initiated at the same time and the initiators provide growing chains of various lengths at any time during the polymerization process. Another reason is that the propagating chains in a free radical process can react with each other in processes known as combination and disproportionation, both of which are irreversibly chain-terminating reaction processes. In doing so, chains of varying lengths are terminated at different times during the reaction process, resulting in resins consisting of polymeric chains which vary widely in length from very small to very large and which thus have broad polydispersities. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. These prior art polymerization processes produce polymers having broad polydispersities and in some instances, low polymerization rates. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4 581 429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O• groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine.

EP-A-735 052 discloses a method of preparing thermoplastic polymers of narrow polydispersities by free radical-initated polymerization, which comprises adding a free radical initiator and a stable free radical agent to the monomer compound.

This method has the disadvantage that uncontrollable recombinations of initiator radicals occur immidiately after their formation, thus producing variable ratios between initiator radicals and stable free radicals. Consequently there is not enough control about the polymerization process.

There is therefore still a need for polymerization processes for the preparation of narrow polydispersity polymeric resins with defined molecular weights using the economical free radical polymerization techniques. These polymerization processes will also control the physical properties of the polymers such as viscosity, hardness, gel content, processability, clarity, high gloss, durability, and the like.

The polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink additives used for electrophotographic imaging processes.

Surprisingly, it has now been found that it is possible to overcome the afore mentioned shortcomings of the prior art by providing a polymerizable composition containing specific initiator compounds. The majority of these compounds are novel and they are also an object of the present invention. Polymerization of the composition results in a polymer or copolymer of narrow polydispersity and a high monomer to polymer conversion even at relatively low temperatures and at short reaction times, making the polymerization process particularly suitable for industrial applications. The resulting copolymers are of high purity and in many cases colourless, therefore not requiring any further purification.

One object of the present invention is to provide a polymerizable composition, comprising
a) at least one ethylenically unsaturated monomer or oligomer, and
b) an initiator compound of formula (I)

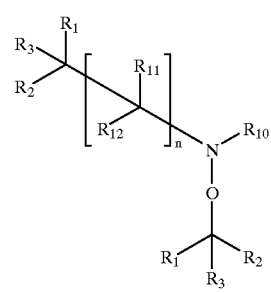

(I)

wherein n is 0 or 1
$R_1$, $R_2$, $R_3$ are each independently of one another hydrogen, halogen, $NO_2$, cyano, $-CONR_5R_6$, $-(R_9)COOR_4$, $-C(O)-R_7$, $-OR_8$, $-SR_8$, $-NHR_8$, $-N(R_8)_2$, carbamoyl, di($C_1$-$C_{18}$alkyl)carbamoyl, $-C(=NR_5)(NHR_6)$;

unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_2$ and $R_3$, together with the linking carbon atom, form a $C_3$–$C_{12}$ cycloalkyl radical, a ($C_4$–$C_{12}$ cycloalkanon)-yl radical or a $C_3$–$C_{12}$cycloalkyl radical containing at least one O atom and/or a $NR_8$ group; or if n is 1

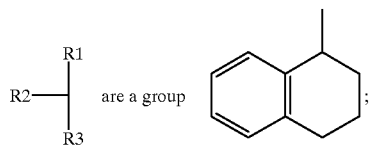

$R_4$ is hydrogen, $C_1$–$C_{18}$alkyl, phenyl, an alkali metal cation or a tetraalkylammonium cation; $R_5$ and $R_6$ are hydrogen, $C_1$–$C_{18}$alkyl, $C_2$–$C_{18}$alkyl which is substituted by at least one hydroxy group or, taken together, form a $C_2$–$C_{12}$alkylene bridge or a $C_2$–$C_{12}$-alkylene bridge interrupted by at least one O or/and $NR_8$ atom;

$R_7$ is hydrogen, $C_1$–$C_{18}$alkyl or phenyl;

$R_8$ is hydrogen, $C_1$–$C_{18}$alkyl or $C_2$–$C_{18}$alkyl which is substituted by at least one hydroxy group;

$R_9$ is $C_4$–$C_{12}$alkylen or a direct bond;

$R_{10}$ is $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom; or $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl) amino; if n is 1

$R_{11}$ is $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or halogen, cyano, hydroxy, carboxy, $C_1$–$C_4$alkylamino or di($C_1$–$C_4$alkyl)amino; or a polycyclic cycloaliphatic ring system or a polycyclic cycloaliphatic ring system with at least one di- or trivalent nitrogen atom; or $R_{10}$ and $R_{11}$ together form a $C_2$–$C_{12}$alkylene bridge, a $C_3$–$C_{12}$alkylen-on bridge or a $C_2$–$C_{12}$alkylene bridge which is interrupted by at least one O or N atom, which bridges are unsubstituted or substituted with $C_1$–$C_{18}$alkyl, hydroxy ($C_1$–$C_4$)alkyl, phenyl, $C_7$–$C_9$phenylalkyl, $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino, $R_{12}$ is hydrogen, —($R_9$)$COOR_4$, cyano, —$OR_8$, —$SR_8$, —$NHR_8$, —$N(R_8)_2$, —NH—C(O)—$R_8$, $C_3$–$C_{12}$cycloalkyl containing at least one nitrogen or oxygen atom; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino, di($C_1$–$C_4$alkyl)amino; or $R_{11}$ and $R_{12}$ together with the linking carbon atom form a $C_3$–$C_{12}$cycloalkyl radical; with the proviso that bis-(2-cyano-2-propyl)-N-phenylhydroxylamine is excluded and if n=0 $R_{10}$ is different from the group —$CR_1R_2R_3$.

The initiator compound of formula (I) is preferably present in an amount of 0.01 mol-% to 30 mol-%, more preferably in an amount of 0.1 mol-% to 10 mol-% and most preferably in an amount of 0.1 to 5 mol-%, based on the monomer, oligomer or monomer/oligomer mixture used.

Preferably compounds of formula (I) do not contain the structural element 2,2,6,6 tetra($C_1$–$C_4$alkyl)piperidine, 2,2,5,5 tetra($C_1$–$C_4$alkyl)pyrrolidin or 1,1,3,3 tetra($C_1$–$C_4$alkyl)isoindoline Halogen is fluoro, chloro, bromo or iodo.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

The alkenyl radicals in the various substituents may be linear or branched. Examples of $C_2$–$C_{18}$alkenyl are vinyl, allyl, 2-methylallyl, butenyl, hexenyl, undecenyl and octadecenyl. Preferred alkenyls are those, wherein the carbon atom in the 1-position is saturated and where the double bond is not activated by substituents like O, C═O, and the like. Examples of $C_2$–$C_{18}$alkynyl are ethynyl, 2-butynyl, 3-hexynyl, 5-undecynyl, 6-octadecynyl. The alkynyl radicals may be linear or branched.

$C_7$–$C_9$phenylalkyl is for example benzyl, phenylpropyl, α,α-dimethylbenzyl or α-methylbenzyl.

$C_9$–$C_{11}$phenylalkyl is for example α,α-dimethylbenzyl, α,α-metylethylbenzyl or α,α-diethylbenzyl.

$C_3$–$C_{12}$cycloalkyl which is unsubstituted or substituted by 1, 2 or 3 $C_1$–$C_4$alkyl is typically cyclopropyl, cyclopentyl, methylcyclopentyl, dimethylcyclopentyl, cyclohexyl, methylcyclohexyl.

Alkyl substituted by —OH is typically 2-hydroxyethyl, 2-hydroxypropyl or 2-hydroxybutyl.

$C_1$–$C_{18}$Alkyl substituted by $C_1$–$C_{18}$alkoxy, preferably by $C_1$–$C_4$alkoxy, in particular by methoxy or ethoxy, is typically 2-methoxyethyl, 2-ethoxyethyl, 3-methoxypropyl, 3-ethoxypropyl, 3-butoxypropyl, 3-octoxypropyl and 4-methoxybutyl.

$C_1$–$C_{18}$Alkyl substituted by di($C_1$–$C_4$alkyl)amino is preferably e.g. dimethylamino, diethylamino, 2-dimethylaminoethyl, 2-diethylaminoethyl, 3-dimethylaminopropyl, 3-diethylaminopropyl, 3-dibutylaminopropyl and 4-diethylaminobutyl.

$C_1$–$C_{18}$Alkyl substituted by $C_1$–$C_4$alkylamino is preferably e.g. methylamino, ethylamino, 2-methylaminoethyl, 2-ethylaminoethyl, 3-methylaminopropyl, 3-ethylaminopropyl, 3-butylaminopropyl and 4-ethylaminobutyl.

$C_1$–$C_8$Alkoxy and, preferably $C_1$–$C_4$alkoxy, are typically methoxy, ethoxy, propoxy, isopropoxy, butoxy, isobutoxy, pentoxy, isopentoxy, hexoxy, heptoxy or octoxy.

$C_1$–$C_4$Alkylthio is typically thiomethyl, thioethyl, thiopropyl, thioisopropyl, thiobutyl and thioisobutyl.

$C_3$–$C_{12}$cycloalkyl interrupted by at least on nitrogen or oxygen atom is typically oxiran, 1,4-dioxane, tetrahydrofuran, γ-butyrolactone, ε-caprolactam, oxirane, aziridine, diaziridine, pyrrole, pyrrolidine, thiophen, furan, pyrazole, imidazole, oxazole, oxazolidine, thiazole, pyran, thiopyran, piperidine or morpholine.

Examples of $C_2$–$C_{12}$alkylene bridges, preferably of $C_2$–$C_6$alkylene bridges, are ethylene, propylene, butylene, pentylene, hexylene.

$C_2$–$C_{12}$alkylene bridges interrupted by at least one N or O atom are, for example, —$CH_2$—O—$CH_2$—$CH_2$—, —$CH_2$—O—$CH_2$—$CH_2$—, —$CH_2$—O—$CH_2$—$CH_2$—$CH_2$—$CH_2$—, —$CH_2$—O—$CH_2$—$CH_2$—O—$CH_2$—, —$CH_2$—NH—$CH_2$—$CH_2$—, —$CH_2$—NH—$CH_2$—$CH_2$—$CH_2$—, —$CH_2$—NH—$CH_2$—$CH_2$—$CH_2$—$CH_2$—, —$CH_2$—NH—$CH_2$—$CH_2$—NH—$CH_2$— or —$CH_2$—NH—$CH_2$—$CH_2$—O—CH2—.

Examples for $C_4$–$C_{12}$cycloalkanone-yl are cyclopentanone-yl, cyclohexanone-yl or cycloheptanone-yl.

Phenyl substituted by 1, 2 or 3 $C_1$–$C_4$alkyl or $C_1$–$C_4$alkoxy is typically methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of polycyclic cycloaliphatic ring systems are adamantane, cubane, twistane, norbornane, bycyclo[2.2.2]octane or bycyclo[3.2.1]octane.

An example of a polycyclic heterocycloaliphatic ring system is hexamethylentetramine (urotropine).

The C-atom to which the substituents $R_1$, $R_2$ and $R_3$ are bound is preferably a secondary or tertiary C-atom more preferably it is a tertiary C-atom.

Examples for $C_4$–$C_{18}$alkyl bound via a tertiary C-atom to the nitrogen atom are the following groups:

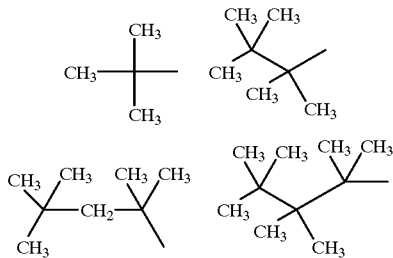

The monomers suitable for use in the present invention may be water-soluble or water-insoluble. Water soluble monomers contain typically a carboxylic acid group or a salt of a carboxylic acid group. Water insoluble monomers are typically free of acid and phenolic groups.

Typical monoethylenically unsaturated monomers free of carboxylic acid which are suitable for this invention include the alkyl esters of acrylic or methacrylic acids such as methyl acrylate, ethyl acrylate, butyl acrylate, methyl methacrylate, ethyl methacrylate, butyl methacrylate and isobutyl methacrylate; the hydroxyalkyl esters of acrylic or methacrylic acids, such as hydroxyethyl acrylate, hydroxypropyl acrylate, hydroxyethyl methacrylate, and hydroxypropyl methacrylate; acrylamide, methacrylamide, N-tertiary butylacrylamide, N-methylacrylamide, N,N-dimethylacrylamide; acrylonitrile, methacrylonitrile, allyl alcohol, dimethylaminoethyl acrylate, dimethylaminoethyl methacrylate, phosphoethyl methacrylate, N-vinylpyrrolidone, N-vinylformamide, N-vinylimidazole, vinyl acetate, conjugated dienes such as butadiene or isoprene, styrene, styrenesulfonic acid salts, vinylsulfonic or 2-acrylamido-2-methylpropane-sulfonic acid salts and acryloyl chloride.

The polymerizable composition of the present invention may additionally comprise a solvent selected from the group consisting of water, alcohols, esters, ethers, ketones, amides, sulfoxides, hydrocarbons and halogenated hydrocarbons.

Preferred ethylenically unsaturated monomers or oligomers are selected from the group consisting of styrene, substituted styrene, conjugated dienes, acrolein, vinyl acetate, (alkyl)acrylic acidanhydrides, (alkyl)acrylic acid salts, (alkyl)acrylic esters or (alkyl)acrylamides.

Particularly preferred ethylenically unsaturated monomers are styrene, α methyl styrene, ρ-methyl styrene or a compound of formula $CH_2$=C($R_a$)—(C=Z)—$R_b$, wherein $R_a$ is hydrogen or $C_1$–$C_4$alkyl, $R_b$ is $NH_2$, O(Me), glycidyl, unsubstituted $C_1$–$C_{18}$alkoxy or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino;

Me is a monvalent metal atom and

Z is oxygen or sulfur.

Typical metal atoms are Na, K or Li.

Examples and preferences for alkyl, alkoxy, alkylamino, dialkylamino and hydroxy-substituted alkoxy are afore mentioned.

In a particular preferred composition $R_a$ is hydrogen or methyl, $R_b$ is $NH_2$, glycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino;and Z is oxygen.

Most preferred is a polymerizable composition, wherein the ethylenically unsaturated monomer is methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide or methacrylamide.

Examples of comonomers suitable for use in the present invention are $C_3$–$C_6$ethylenically unsaturated monocarboxylic acids as well as the alkali metal salts and ammonium salts thereof. The $C_3$–$C_6$ethylenically unsaturated monocarboxylic acids include acrylic acid, methacrylic acid, crotonic acid, vinylacetic acid and acryloxypropionic acid. Acrylic acid and methacrylic acid are the preferred monoethylenically unsaturated monocarboxylic acid monomers.

Examples for $C_8$–$C_{16}$ ethylenically unsaturated phenolics, which may also be used as comonomers include 4-hydroxy styrene, 4-hydroxy, α-methyl styrene, and 2,6-ditert. butyl, 4-vinyl phenol.

Another class of carboxylic acid monomers suitable for use as comonomers in this invention are $C_4$–$C_6$-ethylenically unsaturated dicarboxylic acids and the alkali metal and ammonium salts thereof as well as the anhydrides of the cis-dicarboxylic acids. Suitable examples include maleic acid, maleic anhydride, itaconic acid, mesaconic acid, fumaric acid and citraconic acid. Maleic anhydride and itaconic acid are the preferred monoethylenically unsaturated dicarboxylic acid monomer(s).

The acid monomers suitable for use in this invention may be in their acid forms or in the form of the alkali metal salts or ammonium salts of the acid. Suitable bases useful for neutralizing the monomer acids include sodium hydroxide, ammonium hydroxide, potassium hydroxide, and the like. The acid monomers may be neutralized to a level of from 0 to 50% and, preferably, from 0 to about 20%. In many cases, the carboxylic acid monomers may be used in the completely neutralized form. The monomers may be neutralized prior to or during polymerization.

Preferred are neutralized carboxylic acid monomers or anhydrides.

Preferred initiator compounds are those, wherein n is 0 or 1;

$R_1$, $R_2$, $R_3$ are each independently of one another $NO_2$, cyano, —($R_9$)COO$R_4$, —CON$R_5R_6$, —C(O)—$R_7$, —O$R_8$, carbamoyl, di($C_1$–$C_{18}$alkyl)carbamoyl, —C(=N$R_5$)(NH$R_6$); unsubstituted $C_1$–$C_{18}$alkyl, $C_7$–$C_9$phenylalkyl or $C_3$–$C_{12}$cycloalkyl; or $C_1$–$C_{18}$alkyl, $C_7$–$C_9$phenylalkyl or $C_3$–$C_{12}$cycloalkyl, which are substituted by amino, hydroxy, cyano, carboxy, $C_1$–$C_4$alkoxy, $C_1$–$C_4$alkylamino or di($C_1$–$C_4$alkyl)amino; or phenyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or $R_2$ and $R_3$, together with the linking carbon atom, form a $C_3$–$C_{12}$ cycloalkyl radical; $R_4$ is, $C_1$–$C_{18}$alkyl, phenyl, an alkali metal cation or a tetraalkylammonium cation; $R_5$ and $R_6$ are hydrogen, $C_1$–$C_{18}$alkyl, $C_2$–$C_{18}$alkyl which is substituted by at least one hydroxy group or, taken together, form a $C_2$–$C_{12}$alkylene bridge; $R_7$ is hydrogen, $C_1$–$C_{18}$alkyl or phenyl;

$R_8$ is $C_1$–$C_{18}$alkyl or $C_2$–$C_{18}$alkyl which is substituted by at least one hydroxy group; and $R_9$ is $C_1$–$C_4$alkylen or a direct bond.

$R_{10}$ is $C_4$–$C_{18}$alkyl bound via a tertiary C-atom to the nitrogen atom, phenyl, $C_9$–$C_{11}$phenylalkyl or $C_3$–$C_{12}$cycloalkyl;

if n is 1

$R_{11}$ is $C_1$–$C_{18}$alkyl, $C_7$–$C_9$phenylalkyl or $C_3$–$C_{12}$cycloalkyl or $R_{10}$ and $R_{11}$ together form a $C_2$–$C_{12}$alkylene bridge or a $C_2$–$C_{12}$alkylene bridge which is interrupted by at least one O or N atom, which bridges are unsubstituted or substituted with $C_1C_{18}$alkyl;

$R_{12}$ is, unsubstituted $C_1$–$C_{18}$alkyl, phenyl, $C_7$–$C_9$phenylalkyl or $C_3$–$C_{12}$cycloalkyl or $R_{11}$ and $R_{12}$ together with the linking carbon atom, form a $C_3$–$C_{12}$ cycloalkyl radical.

More preferred are initiators, wherein n is 0 or 1;

$R_1$, $R_2$, $R_3$ are each independently of one another $NO_2$, cyano, —($R_9$)COO$R_4$, —CON$R_5R_6$, —C(O)—$R_7$, —O$R_8$, carbamoyl, di($C_1$–$C_8$alkyl)carbamoyl, —C(=N$R_5$)(NH$R_6$); unsubstituted $C_1$–$C_{12}$alkyl, $C_7$–$C_9$phenylalkyl or $C_5$–$C_7$cycloalkyl; or $C_1$–$C_8$alkyl, $C_7$–$C_9$phenylalkyl or $C_5$–$C_7$cycloalkyl or, which are substituted by amino, hydroxy, cyano, carboxy, $C_1$–$C_4$alkoxy, $C_1$–$C_4$alkylamino or di($C_1$–$C_4$alkyl)amino; or phenyl, or $R_2$ and $R_3$, together with the linking carbon atom, form a $C_5$–$C_7$cycloalkyl radical;

$R_4$ is $C_1$–$C_8$alkyl, phenyl, an alkali metal cation or a tetraalkylammonium cation;

$R_5$ and $R_6$ are hydrogen, $C_1$–$C_8$alkyl, $C_2$–$C_8$alkyl which is substituted by at least one hydroxy group or, taken together, form a $C_2$–$C_6$alkylene bridge;

$R_7$ is hydrogen, $C_1$–$C_8$alkyl or phenyl;

$R_8$ is $C_1$–$C_8$alkyl or $C_2$–$C_8$alkyl which is substituted by at least one hydroxy group;

$R_9$ is $C_1$–$C_4$alkylen or a direct bond;

$R_{10}$ is $C_4$–$C_{18}$alkyl bound via a tertiary C-atom to the nitrogen atom or phenyl;

if n is 1

$R_{11}$ is $C_1$–$C_{18}$alkyl, phenyl or $C_7$–$C_9$phenylalkyl or $R_{10}$ and $R_{11}$ together form a $C_2$–$C_{12}$alkylene bridge or a $C_2$–$C_{12}$alkylene bridge which is interrupted by at least one O or N atom, which bridges are unsubstituted or substituted with $C_1$–$C_{18}$alkyl;

$R_{12}$ is unsubstituted $C_1$–$C_{18}$alkyl or phenyl.

Particularly preferred initiators are those, wherein n is 0 or 1;

$R_1$, $R_2$, $R_3$ are each independently of one another $NO_2$, cyano, —C(O)—$R_7$, —O$R_8$, unsubstituted $C_1$–$C_{12}$alkyl or phenyl, which is unsubstituted or substituted by $C_1$–$C_4$alkyl, $C_1$–$C_4$alkoxy, cyano, hydroxy, carboxy, $C_1$–$C_4$alkylamino or di($C_1$–$C_4$alkyl)amino;

or $R_2$ and $R_3$, together with the linking carbon atom, form a $C_5$–$C_7$ cycloalkyl radical;

$R_8$ is $C_1$–$C_8$alkyl or $C_2$–$C_8$alkyl which is substituted by at least one hydroxy group and $R_{10}$ is $C_4$–$C_{18}$alkyl bound via a tertiary C-atom to the nitrogen atom, phenyl or $C_9$–$C_{11}$phenylalkyl;

if n is 1

$R_{11}$ is $C_1$–$C_{12}$alkyl; or $R_{10}$ and $R_{11}$ together form a $C_2$–$C_6$alkylene bridge which is unsubstituted or substituted with $C_1$–$C_4$alkyl;

$R_{12}$ is hydrogen, unsubstituted $C_1$–$C_4$alkyl or phenyl.

Preferably n is 0; $R_1$ is cyano; $R_2$ and $R_3$ are each independently of one another unsubstituted $C_1$–$C_{12}$alkyl or phenyl; or $R_2$ and $R_3$, together with the linking carbon atom, form a $C_5$–$C_7$cycloalkyl radical; $R_{10}$ is $C_4$–$C_{12}$alkyl bound via a tertiary C-atom to the nitrogen atom, $C_9$–$C_{11}$phenylalkyl or phenyl.

Another preferred group is wherein n is 1 $R_1$ is cyano; $R_2$ and $R_3$ are each independently of one another unsubstituted $C_1$–$C_{12}$alkyl or phenyl;

or $R_2$ and $R_3$, together with the linking carbon atom, form a $C_5$–$C_7$ cycloalkyl radical;

$R_{10}$ is $C_4$–$C_{12}$alkyl bound via a tertiary C-atom to the nitrogen atom, $C_9$–$C_{11}$phenylalkyl or phenyl; or $R_{10}$ and $R_{11}$ together form a $C_2$–$C_6$alkylene bridge which is unsubstituted or substituted with $C_1$–$C_4$alkyl; and $R_{12}$ is $C_1$–$C_4$alkyl.

This invention also relates to a free radical polymerization process and polymers obtained thereby, which process overcomes many of the problems and disadvantages of the afore mentioned prior art processes.

This process is used for preparing an oligomer, a cooligomer, a polymer or a copolymer -block or random- by free radical polymerization of at least one ethylenically unsaturated monomer or oligomer, which comprises (co)polymerizing the monomer or monomers/oligomers in the presence of an initiator compound of formula (I)

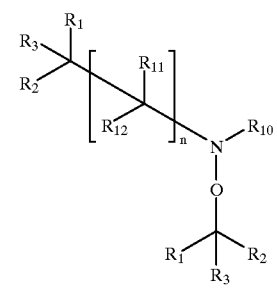

(I), under reaction conditions capable of effecting scission of the O—C bond to form two free radicals, the radical •C$R_1R_2R_3$ being capable of initiating polymerization.

Preferably, the scission of the O—C bond is effected by heating, ultrasonic treatment or exposure to actinic radiation.

To perform the scission of the O—C bond by heating, the temperature is particularly preferably raised to more than 50° C. and less than 160° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The initiator compound is preferably present in an amount of 0.01 mol-% to 30 mol-%, more preferably in an amount of 0.1 mol-% to 10 mol-% and most preferably in an amount of 0.1 mol-% to 5 mol-%, based on the monomer or monomer mixture used.

When monomer mixtures or monomer/oligomer mixtures are used, the calculation of mol-% is based on an average molecular weight of the mixture.

Hydrophilic monomers, polymers and copolymers of the present invention can be separated from one another or from the polymerization reaction mixture by, for example, changing the pH of the reaction media and by other well known conventional separation techniques.

The polymerization temperature may range from about 50° C. to about 180° C., preferably from about 80° C. to about 150° C. At temperatures above about 180° C., the controlled conversion of the monomer into polymer decreases, and uncertain and undesirable by-products like thermally initiated polymer are formed or destruction of the polymerization regulator may occur. Frequently, these by-products discolor the polymer mixture and a purification step may be required to remove them, or they may be intractable.

Therefore the surprisingly high reactivity of the present initiators which are already active at relatively low temperatures leads to short reaction times. The resulting polymers are usually colourless and they can be used in most cases without any further purification step. This is an important advantage when industrial scale-up is considered.

After the polymerizing step is complete, the formed (co)polymer obtained is isolated. The isolating step of the present process is conducted by known procedures, e.g. by distilling off the unreacted monomer or by precipitation in a suitable nonsolvent, filtering the precipitated polymer followed by washing and drying the polymer.

Yet another embodiment of this invention is a process for preparing a block copolymer involving at least two stages, which comprises forming a polymer with alkoxyamine end groups of the general structure of formula II

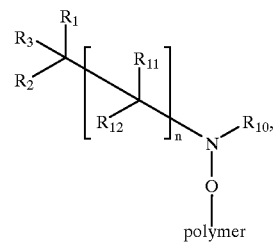

wherein n, $R_1$, $R_2$, $R_3$, $R_{10}$ $R_{11}$ and $R_{12}$ are as defined above, the polymer containing the initiator group —$CR_1R_2R_3$ and having the oxyamine group essentially attached as terminal group, and adding a further monomer followed by heating to form a block copolymer.

The homopolymers or copolymers may also be prepared in a so called in "situ process", which means that the compounds of formula (I) are prepared from a radical •$CR_1R_2R_3$ and a compound of formula $R_{10}NO$ or

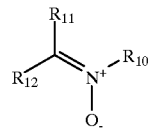

in the presence of an ethylenically unsaturated monomer or oligomer. The radical •$CR_1R_2R_3$ itself may be prepared as described below, preferably from a compound which liberates the radical upon heating. Under such conditions formation of the compounds of formula (I), their scission and polymerization occur simultaneously. By changing the reaction temperature different pathways of the reaction are favored. It is important to note, that under such reaction conditions still high conversion rates in short reaction times and low polydispersities are achieved.

It is also possible to add the ethylenically unsaturated monomer or oligomer subsequently to the mixture of a radical initiator and a compound of formula $R_{10}NO$ or

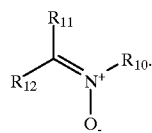

In this case a compound of formula (I) is prepared to a certain amount, which may be up to 100% and subsequently the monomer is added without further isolating the compound of formula (I).

Therefore another object of the invention is a process for preparing an oligomer, a cooligomer, a polymer or a copolymer (block or random) by free radical polymerization of at least one ethylenically unsaturated monomer or oligomer, which comprises generating a free radical •$CR_1R_2R_3$ (V) from a compound capable of eliminating a neutral molecule, or undergoing C—C bond-scission upon thermal or photochemical treatment, or by hydrogen abstraction from a compound $R_1R_2R_3C$—H in reaction with reactive radicals, and reacting the free radical •$CR_1R_2R_3$ (V) with a compound $R_{10}$NO or

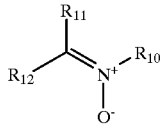

in a solvent which does not interfere with the radical reaction in the presence of at least one ethylenically unsaturated monomer or oligomer.

Suitable monomers are those mentioned above. The polymer of formula (II) may be isolated prior to the next reaction step or it may be used without isolation, and the second monomer is added to the reaction mixture of the first step.

Block copolymers are, for example, block copolymers of polystyrene and polyacrylate (e.g., Poly(styrene-co-acrylate) or Poly(styrene-co-acrylate-co-styrene). They are usefull as adhesives or as compatibilizers for polymer blends or as polymer toughening agents. Poly(methylmethacrylate-co-acrylate) diblock copolymers or Poly(methylacrylate-co-acrylate-co-methacrylate) triblock copolymers) are useful as dispersing agents for coating systems, as coating additives (e.g. rheological agents, compatibilizers, reactive diluents) or as resin component in coatings(e.g. high solid paints) Block copolymers of styrene, (meth)acrylates and/or acrylonitrile are useful plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1000 to 400000 g/mol, preferably from 2000 to 250000 g/mol and, more preferably, from 2000 to 200000 g/mol. When produced in bulk, the number average molecular weight may be up to 500000 (with the same minimum weights as mentioned above). The number average molecular weight may be determined by size exclusion chromatography (SEC), gel permeation chromatography (GPC), matrix assisted laser desorption/ionizabon mass spectrometry (MALDI-MS) or, if the initiator carries a group which can be easily distinguished from the monomer(s), by NMR spectroscopy or other conventional methods.

The (co)polymers of the present invention typically have a low polydispersity. Preferably the polydispersity is from 1.1 to 2.2, more preferably from 1.1 to 1.9 and most preferably from 1.2 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers. Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)-acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macrmolecules 1996, Vol 29, No.12, pages 4167–4171, graft (co)polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

Yet another object of the present invention is a polymer or oligomer, having at least one initiator group —$CR_1R_2R_3$ and at least one oxyamine group of formula (IIa)

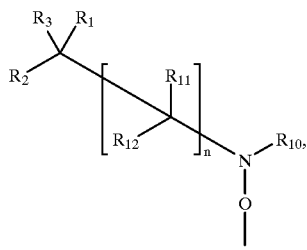

(IIa)

wherein n, $R_1$, $R_2$, $R_3$, $R_{10}$ $R_{11}$ and $R_{12}$ have the meanings and preferred meanings as defined above, obtainable by the process as defined above.

In another of its aspects, this invention relates to a compound of formula (I)

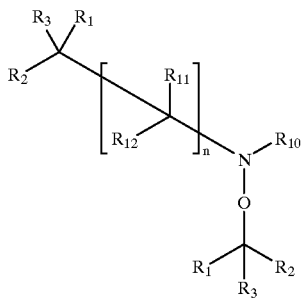

(I)

wherein n is 0 or 1
$R_1$, $R_2$, $R_3$ are each independently of one another hydrogen, halogen, $NO_2$, cyano, $-CONR_5R_6$, $-(R_9)COOR_4$, $-C(O)-R_7$, $-OR_8$, $-SR_8$, $-NHR_8$, $-N(R_8)_2$, carbamoyl, di($C_1-C_{18}$alkyl)carbamoyl, $-C(=NR_5)(NHR_6)$;
unsubstituted $C_1-C_{18}$alkyl, $C_2-C_{18}$alkenyl, $C_2-C_{18}$alkynyl, $C_7-C_9$phenylalkyl, $C_3-C_{12}$cycloalkyl or $C_3-C_{12}$cycloalkyl containing at least one nitrogen or oxygen atom; or
$C_1-C_{18}$alkyl, $C_2-C_{18}$alkenyl, $C_2-C_{18}$ alkynyl, $C_7-C_9$phenylalkyl, $C_3-C_{12}$cycloalkyl or $C_3-C_{12}$cycloalkyl containing at least one nitrogen or oxygen atom, which are substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; or
phenyl, naphthyl, which are unsubstituted or substituted by $C_1-C_4$alkyl, $C_1-C_4$alkoxy, $C_1-C_4$alkylthio, halogen, cyano, hydroxy, carboxy, $C_1-C_4$alkylamino or di($C_1-C_4$alkyl)amino; or $R_2$ and $R_3$, together with the linking carbon atom, form a $C_3-C_{12}$ cycloalkyl radical, a ($C_4-C_{12}$ cycloalkanon)-yl radical or a $C_3-C_{12}$cycloalkyl radical containing at least one O atom and/or a $NR_8$ group; or if n is 1

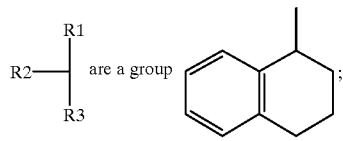

$R_4$ is hydrogen, $C_1-C_{18}$alkyl, phenyl, an alkali metal cation or a tetraalkylammonium cation;
$R_5$ and $R_6$ are hydrogen, $C_1-C_{18}$alkyl, $C_2-C_{18}$alkyl which is substituted by at least one hydroxy group or, taken together, form a $C_2-C_{12}$alkylene bridge or a $C_2-C_{12}$-alkylene bridge interrupted by at least one O or/and $NR_8$ atom;

$R_7$ is hydrogen, $C_1-C_{18}$alkyl or phenyl;
$R_8$ is hydrogen, $C_1-C_{18}$alkyl or $C_2-C_{18}$alkyl which is substituted by at least one hydroxy group;
$R_9$ is $C_1-C_{12}$alkylen or a direct bond;
$R_{10}$ is $C_4-C_{18}$alkyl bound via a tertiary C-atom to the nitrogen atom, $C_9-C_{11}$phenylalkyl, $C_3-C_{12}$cycloalkyl or $C_3-C_{12}$cycloalkyl containing at least one nitrogen or oxygen atom; or $C_4-C_{18}$alkyl bound via a tertiary C-atom to the nitrogen atom, $C_9-C_{11}$phenylalkyl, $C_3-C_{12}$cycloalkyl or $C_3-C_{12}$cycloalkyl containing at least one nitrogen or oxygen atom, which are substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; or
phenyl, naphthyl, which are unsubstituted or substituted by $C_1-C_4$alkyl, $C_1-C_4$alkoxy, $C_1-C_4$alkylthio, halogen, cyano, hydroxy, carboxy, $C_1-C_4$alkylamino or di($C_1-C_4$alkyl)amino; or a polycyclic cycloaliphatic ring system or a polycyclic cycloaliphatic ring system with at least one di- or trivalent nitrogen atom;
if n is 1 one nitrogen or oxygen atom; or
$C_1-C_{18}$alkyl, $C_7-C_9$phenylalkyl, $C_3-C_{12}$cycloalkyl or $C_3-C_{12}$cycloalkyl containing at least one nitrogen or oxygen atom, which are substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; or phenyl, naphthyl, which are unsubstituted or substituted by $C_1-C_4$alkyl, $C_1-C_4$alkoxy, $C_1-C_4$alkylthio, halogen, cyano, hydroxy, carboxy, $C_1-C_4$alkylamino or di($C_1-C_4$alkyl)amino; or a polycyclic cycloaliphatic ring system or a polycyclic cycloaliphatic ring system with at least one di- or trivalent nitrogen atom; or
$R_{10}$ and $R_{11}$ together form a $C_2-C_{12}$alkylene bridge, a $C_3-C_{12}$alkylen-on bridge or a $C_2-C_{12}$alkylene bridge which is interrupted by at least one O or N atom, which bridges are unsubstituted or substituted with $C_1-C_{18}$alkyl, hydroxy($C_1-C_4$)alkyl, phenyl, $C_7-C_9$phenylalkyl, $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino, or
$R_{12}$ is hydrogen, $-(R_9)COOR_4$, cyano, $-OR_8$, $-SR_8$, $-NHRa$, $-N(R_8)_2$, $-NH-C(O)-R_8$, unsubstituted $C_1-C_{18}$alkyl, $C_2-C_{18}$alkenyl, $C_2-C_{18}$alkynyl, $C_7-C_9$phenylalkyl, $C_3-C_{12}$cycloalkyl or $C_3-C_{12}$cycloalkyl containing at least one nitrogen or oxygen atom; or
$C_1-C_{18}$alkyl, $C_2-C_{18}$alkenyl, $C_2-C_{18}$ alkynyl, $C_7-C_9$phenylalkyl, $C_3-C_{12}$cycloalkyl or $C_3-C_{12}$cycloalkyl containing at least one nitrogen or oxygen atom, which are substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; or
phenyl, naphthyl, which are unsubstituted or substituted by $C_1-C_4$alkyl, $C_1-C_4$alkoxy, $C_1-C_4$alkylthio, halogen, cyano, hydroxy, carboxy, $C_1-C_4$alkylamino, di($C_1-C_4$alkyl)amino; or $R_{11}$ and $R_{12}$ together with the linking carbon atom, form a $C_3-C_{12}$ cycloalkyl radical;
with the proviso that
if n is 0 $R_{10}$ is different from the group $-CR_1R_2R_3$, and if $R_1$ is CN and $R_2$ and $R_3$ are methyl, $R_{10}$ is not phenyl, phenyl substituted by methyl, 2,4,6-trimethyl, chlor, fluor, (3-methyl,4-fluor), (3-fluor, 4-methyl), (4-fluor, 2-methyl), (4-fluor, 2-methoxy), (2-fluor, 3,5-methyl), 2,5-di-tert.butyl, nitro, 3,5-dinitro or 2 $(-O-C(CH_3)_2CN)$ 4-nitro; and
if n is 1, $R_{12}$ is hydrogen, $R_{10}$ phenyl or benzyl and $R_{11}$ yl, $R_1$, $R_2$ and $R_3$ are not a group $-C(CH_3)_2CN$, $-C(CH_3)_2COOCH_3$, benzyl, methylbenzyl, dimethylbenzyl,

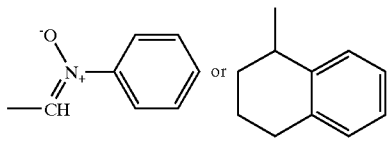

and the compound according to formula I is not

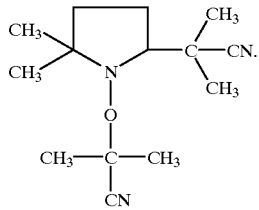

Preferred compounds are those wherein n is 0 or 1;

$R_1$, $R_2$, $R_3$ are each independently of one another $NO_2$, cyano, —C(O)—$R_7$, —$OR_8$, unsubstituted $C_1$–$C_{12}$alkyl or phenyl, which is unsubstituted or substituted by $C_1$–$C_4$alkyl, $C_1$–$C_4$alkoxy, cyano, hydroxy, carboxy, $C_1$–$C_4$alkylamino or di($C_1$–$C_4$alkyl)amino;

or $R_2$ and $R_3$, together with the linking carbon atom, form a $C_5$–$C_7$ cycloalkyl radical;

$R_7$ is, $C_1$–$C_8$alkyl or phenyl;

$R_8$ is $C_1$–$C_8$alkyl or $C_2$–$C_8$alkyl which is substituted by at least one hydroxy group and $R_{10}$ is $C_4$–$C_{18}$alkyl bound via a tertiary C-atom to the nitrogen atom, phenyl or $C_9$–$C_{11}$phenylalkyl;

if n is 1

$R_{11}$ is $C_1$–$C_{18}$alkyl, $C_7$–$C_9$phenylalkyl or $C_3$–$C_{12}$cycloalkyl or $R_{10}$ and $R_{11}$ together form a $C_2$–$C_6$alkylene bridge which is unsubstituted or substituted with $C_1$–$C_4$alkyl;

$R_{12}$ is, unsubstituted $C_1$–$C_4$alkyl or phenyl.

Particularly preferred are compounds wherein n is 0;

$R_1$ is cyano;

$R_2$ and $R_3$ are each independently of one another unsubstituted $C_1$–$C_{12}$alkyl or phenyl; or $R_2$ and $R_3$, together with the linking carbon atom, form a $C_5$–$C_7$ cycloalkyl radical; $R_{10}$ is $C_4$–$C_{12}$alkyl bound via a tertiary C-atom to the nitrogen atom or $C_9$–$C_{11}$iphenylalkyl.

Another particularly preferred group of compounds are those wherein n is 1;

$R_1$ is cyano;

$R_2$ and $R_3$ are each independently of one another unsubstituted $C_1$–$C_{12}$alkyl or phenyl; or $R_2$ and $R_3$, together with the linking carbon atom, form a $C_5$–$C_7$ cycloalkyl radical; $R_{10}$ is $C_4$–$C_{12}$alkyl bound via a tertiary C-atom to the nitrogen atom, $C_9$–$C_{11}$phenylalkyl or phenyl; or $R_{10}$ and $R_{11}$ together form a $C_2$–$C_6$alkylene bridge which is unsubstituted or substituted with $C_1$–$C_4$alkyl; and $R_{12}$ is $C_1$–$C_4$alkyl.

Further meanings and preferrences for the different substitutents $R_1$ to $R_{12}$ are mentioned before.

The invention is also directed to a compound of formula (IV)

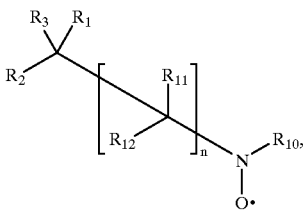

wherein n is 0 or 1

$R_1$, $R_2$, $R_3$ are each independently of one another hydrogen, halogen, $NO_2$, cyano, —$CONR_5R_6$, —($R_9$)$COOR_4$, —C(O)—$R_7$, —$OR_8$, —$SR_8$, —$NHR_8$, —N($R_8$)$_2$, carbamoyl, di($C_1$–$C_{18}$alkyl)carbamoyl, —C(=$NR_5$)(NHR6);

unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl) amino; or $R_2$ and $R_3$, together with the linking carbon atom, form a $C_3$–$C_{12}$ cycloalkyl radical, a ($C_4$–$C_{12}$ cycloalkanon)-yl radical or a $C_3$–$C_{12}$cycloalkyl radical containing at least one O atom and/or a $NR_8$ group; or if n is 1

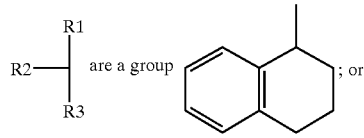

$R_4$ is hydrogen, $C_1$–$C_{18}$alkyl, phenyl, an alkali metal cation or a tetraalkylammonium cation;

$R_5$ and $R_6$ are hydrogen, $C_1$–$C_{18}$alkyl, $C_2$–$C_{18}$alkyl which is substituted by at least one hydroxy group or, taken together, form a $C_2$–$C_{12}$alkylene bridge or a $C_2$–$C_{12}$-alkylene bridge interrupted by at least one O or/and $NR_8$ atom;

$R_7$ is hydrogen, $C_1$–$C_{18}$alkyl or phenyl;

$R_8$ is hydrogen, $C_1$–$C_{18}$alkyl or $C_2$–$C_{18}$alkyl which is substituted by at least one hydroxy group;

$R_9$ is $C_1$–$C_{12}$alkylen or a direct bond;

$R_{10}$ is $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom; or $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl) amino; or a polycyclic cycloaliphatic ring system or a polycyclic cycloaliphatic ring system with at least one di- or trivalent nitrogen atom;

if n is 1

$R_{11}$ is $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl,, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or a polycyclic cycloaliphatic ring system or a polycyclic cycloaliphatic ring system with at least one di- or trivalent nitrogen atom; or $R_{10}$ and $R_{11}$ together form a $C_2$–$C_{12}$alkylene bridge, a $C_3$–$C_{12}$alkylen-on bridge or a $C_2$–$C_{12}$alkylene bridge which is interrupted by at least one O or N atom, which bridges are unsubstituted or substituted with $C_1$–$C_{18}$alkyl, hydroxy ($C_1$–$C_4$)alkyl, phenyl, $C_7$–$C_9$phenylalkyl, $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;

$R_{12}$ is hydrogen, —($R_9$)COOR$_4$, cyano, —OR$_8$, —SR$_8$, —NHR$_8$, —N(R$_8$)$_2$, —NH—C(O)—R$_8$, unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino, di($C_1$–$C_4$alkyl)amino; or $R_{11}$ and $R_{12}$ together with the linking carbon atom, form a $C_3$–$C_{12}$cycloalkyl radical;

with the proviso that if n is 0 $R_{10}$ is different from the group —CR$_1$R$_2$R$_3$, and if $R_1$ is CN and $R_2$ and $R_3$ are methyl, $R_{10}$ is not phenyl, phenyl substituted by methyl, 2,4,6-trimethyl, chlor, fluor, (3-methyl,4-fluor), (3-fluor, 4-methyl), (4-fluor, 2-methyl), (4-fluor, 2-methoxy), (2-fluor, 3,5-methyl), 2,5-di-tert.butyl, nitro, 3,5-dinitro or 2 (—O—C(CH$_3$)$_2$CN) 4-nitro; and if n is 1, $R_{12}$ is hydrogen, $R_{10}$ phenyl or benzyl and $R_{11}$ phenyl, $R_1$, $R_2$ and $R_3$ are not a group —C(CH$_3$)$_2$CN, —C(CH$_3$)$_2$COOCH$_3$, benzyl, methylbenzyl, dimethylbenzyl,

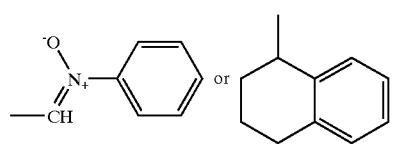 or 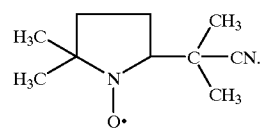

and the compound according to formula IV is not

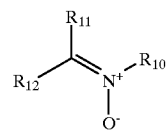

Meanings and preferences for the different substitutents $R_1$ to $R_{12}$ are already mentioned.

A further object of the present invention is a process for preparing a compound of formula (I)

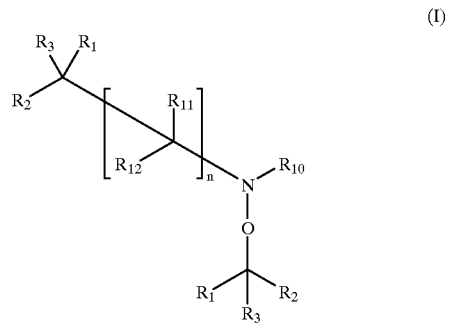

(I)

by generating a free radical •CR$_1$R$_2$R$_3$ (V) from a compound capable of eliminating a neutral molecule, or undergoing C-C bond-scission upon thermal or photochemical treatment, or by hydrogen abstraction from a compound R$_1$R$_2$R$_3$C—H in reaction with reactive radicals, and reacting the free radical •CR$_1$R$_2$R$_3$ (V) with a compound of formula R$_{10}$NO or $$R_{12}\underset{\underset{O^-}{|}}{\overset{R_{11}}{\underset{|}{C}}}=\overset{}{N^+}-R_{10}$$

in a solvent which does not interfere with the radical reaction.

Examples for neutral molecules which can be eliminated are $N_2$ or $O_2$. Reactive radicals which are able to abstract hydrogen are for example alkoxy radicals.

Suitable solvents are aromatic, aliphatic or cycloaliphatic hydrocarbons, such as toluene, benzene xylene, octane or cyclohexane, ethers, such as dioxane, tetrahydrofurane or dibutylether, alcohols, glycols or esters and amides of carboxylic acids.

The free radical •CR$_1$R$_2$R$_3$ is preferably prepared by heating or irradiation of a compound of formula IIIa, IIIb or IIIc

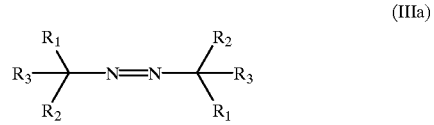

(IIIa)

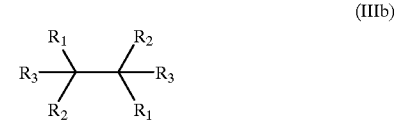

(IIIb)

(IIIc)

Preferably the radical •CR$_1$R$_2$R$_3$ is prepared by a thermal reaction at a temperature from 40° to 150° C., more preferably from 60° to 150° C. and most preferrably from 70° to 140° C. $R_1$, $R_2$ and $R_3$ have the meanings and preferred meanings defined above.

Nitrones of formula (VI) can be prepared according to known methods.

Examples of 5-membered nitrones are for example described by J. B. Bapat and D. St. C. Black in Aust. J. Chem. 21, 2483 (1968). Typical examples are mentioned below.

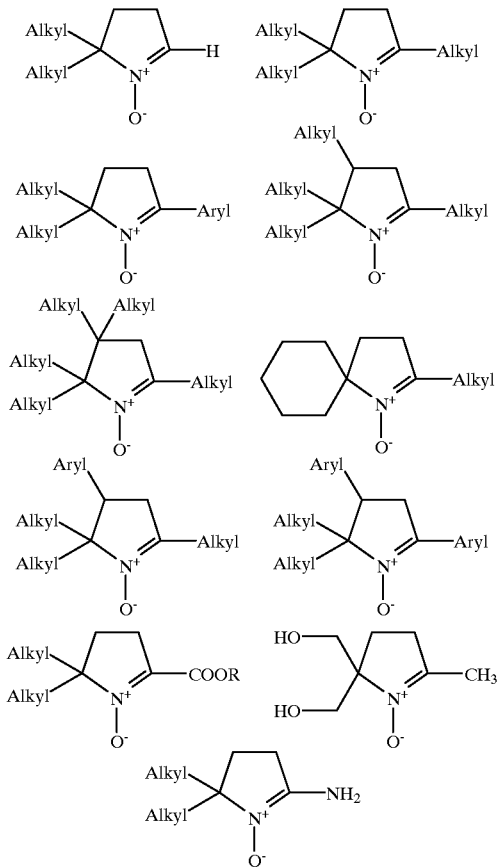

Further nitrones are described by H. Gnichtel, K. E. Schuster in Chem. Ber. 111, 1171 (1978).

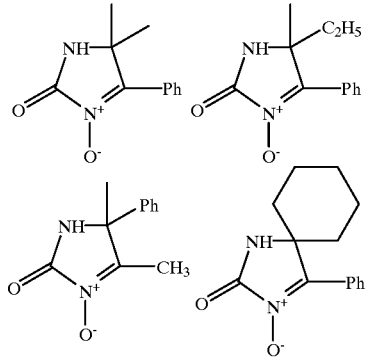

A. G. Krainev, T. D. Williams, D. J. Bigelow describe in J. Magnet. Res., B 111, 272 (1996) the preparation of following nitrones.

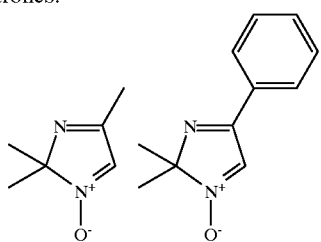

Examples of 6-membered nitrones are for example described by Shun-Ishi Murahashi et al. in J. Org. Chem. 55 1736 (1990).

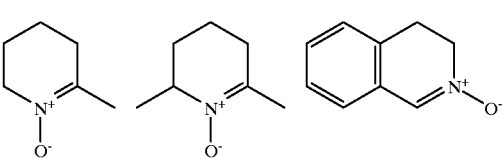

These nitrones may be reacted with the appropriate reactive radical $\bullet CR_1R_2R_3$ to obtain compounds of formula (I).

Some reaction products between nitrones and reactive radicals have been reported and are listed below.

M. Iwamura, N. Inamoto: Bull. Chem. Soc. Japan 43,856 (1970):

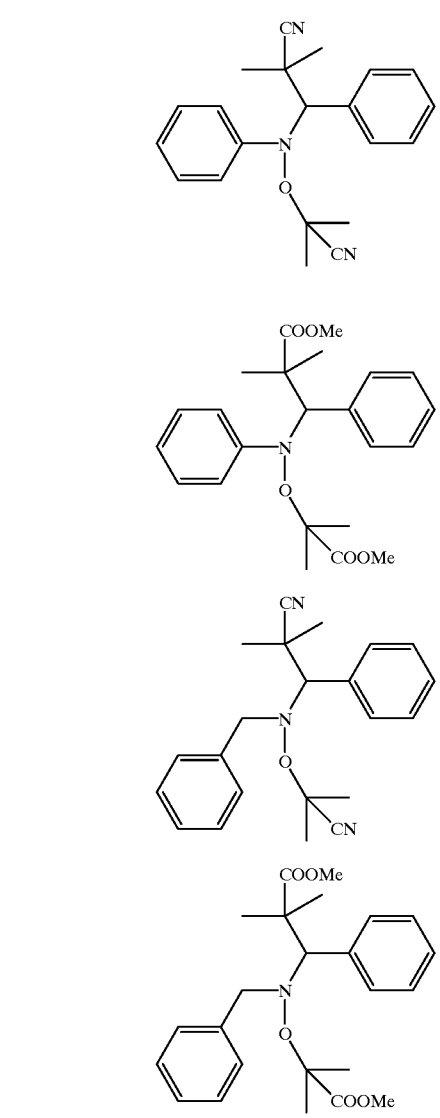

-continued

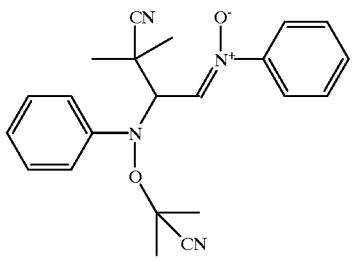

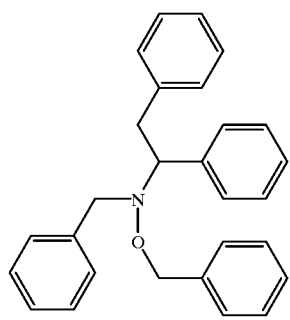

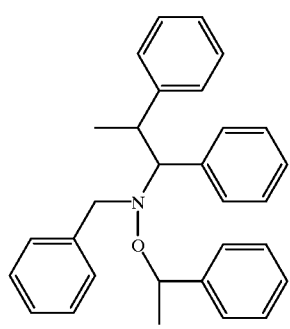

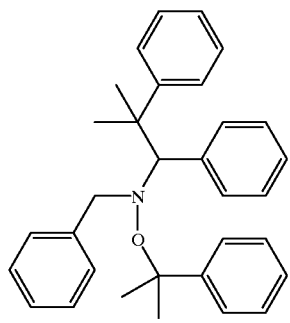

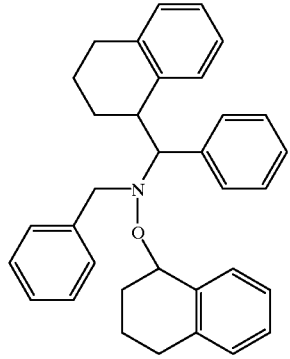

or D. A. Becker: J.Am. Chem. Soc. 118, 905 (1996).

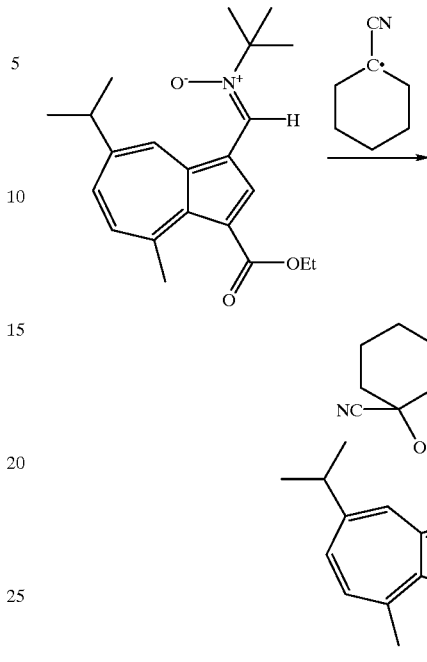

M. Iwamura, N. Inamoto: Bull. Chem. Soc. Japan 43, 860 (1970) have reported the preparation of the following compound.

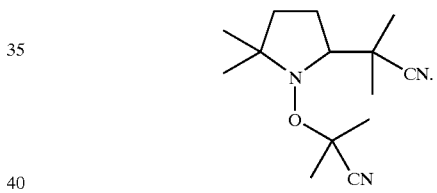

None of these compounds have been used to polymerize ethylenically unsaturated monomers or oligomers.

The production of C-centered radicals is described, inter alia, in Houben Weyl, Methoden der Organischen Chemie, Vol. E 19a, pages 60–147. These methods can be applied in general analogy.

The reaction of reacting radicals with nitroso compounds is known per se and described by B. A. Gingras et al. in J. Chem. Soc. page 1920,1954.

Most preferably, the free radical source is 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide.

These compounds are commercially available.

If more than one radical source is used, a mixture of substitution patterns is obtainable. This invention also relates to the use of an initiator compound of formula (I) for polymerizing ethylenically unsaturated monomers.

The alkoxyamines of formula (I) may be prepared and isolated as described above. However, it is also possible to produce the compounds of formula (I) in situ during polymerization by adding a compound of formula IV, which has been isolated as intermediate in the process described before, to the polymerizable monomers and by adding, also in situ, the corresponding radical initiator.

Consequently a further aspect of the invention is a polymerizable composition, comprising
a) at least one ethylenically unsaturated monomer or oligomer;
b) a compound of formula (IV) and
c) a radical initiator as described above capable of generating a free radical of formula (V)

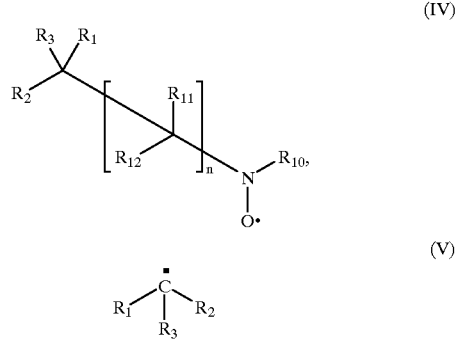

wherein n, $R_1$, $R_2$, $R_3$, $R_{10}$, $R_{11}$ and $R_{12}$ are as defined above including their preferences.

Still another aspect of the invention is a process for preparing an oligomer, a cooligomer, a polymer or a copolymer (block or random) by free radical polymerization of at least one ethylenically unsaturated monomer/oligomer, which comprises subjecting a composition as described above to heat or actinic radiation.

A further aspect of the present invention is the use of a compound of formula I for polymerizing ethylenically unsaturated monomers.

Suitable initiators are those listed above including their preferrences.

The following Examples illustrate the invention in more detail.

A) Examples for the preparation of N,N,O-trisubstituted hydroxylamines (table 1)

Example A1

Preparation of) N-(1,3,3-tetramethyl-butyl)-N,O-bis-(1-cyano-1-methyl-ethyl)-hydroxylamin compound (101)

8,6 g (0,06 mol) 1-nitroso-1,1,3,3-tetramethyl-butan (prepared according to Org. Synth. 65, 166 (1986)) and 24,9 g (0,15 mol) azobis-isobutyronitril are dissolved in 100 ml benzene. After careful purge with argon the solution is refluxed for 2 hours under argon atmosphere. Benzene is distilled off on the rotary evaporator and the residue is diluted with 100 ml hexane. The precipitated 2,3-dimethyl-succinicacid dinitrile was removed by filtration. The filtrate is evaporated and subjected to column chromatography on silica gel (hexane-ethylacetate 9:1). 14,8 g (88%) of the compound of formula (101) are obtained as viscous oil.

Example A2

Preparation of N-(1,1,3,3-tetramethyl-butyl)-N,O-bis-(1-cyano-cyclohexyl)-hydroxylamin (102)

1,4 g (0,01 Mol) 1-nitroso-1,1,3,3-tetramethyl-butan and 4,9 g (0.02 Mol) azobis-(1-cyanocyclohexane) are dissolved in 25 ml chlorbenzene. After careful purge with argon the solution is heated to 100° C. for 3 hours under argon atmosphere. Chlorbenzene is distilled off on the rotary evaporator. The residue subjected to column chromatography on silica gel (hexane/ethylacetate 9:1) and recrystallyzed from hexane. 1.45 g (39%) of the compound of formula (102) are obtained.

TABLE 1

| Nr. | compound | mp. (° C.) | C(%), H(%), N(%) calc./found |
|---|---|---|---|
| 101 | ![structure] | viscous oil | 68.78; 10.46; 15.04/ 68.79; 10.34; 15.04 |
| 102 | ![structure] | 108–112 | 73.49; 10.37; 11.69/ 73.39; 10.43; 11.66 |

TABLE 1-continued

| Nr. | compound | mp. (° C.) | C(%), H(%), N(%) calc./found |
|---|---|---|---|
| 104 | | | |
| V-65 | | | |
| V-70 | | | |

Example A3

Preparation of 1-(1-cyano-1-methyl-ethoxy)-2-(1-cyano-1-methyl-ethyl)-2,5,5-tetra-methyl-pyrrolidin (105)

16 g (0.125 Mol)2,5,5-trimethyl-pyrrolin-1-oxid [prepared according to M. J. Turner et al.: Synth. Commun. 16 (11), 1377 (1986)] and 37 g (0.225 Mol) azobis-isobutyronitril are dissolved in 150 ml benzene. After careful purge with argon the solution is refluxed for 6 hours under argon atmosphere. Benzene is distilled off on the rotary evaporator and the residue is diluted with 100 ml hexane. The precipitated 2,3-dimethyl-succinicacid dinitrile was removed by filtration. The filtrate is evaporated and subjected to column chromatography on silica gel (hexane/ethylacetate 9:1). 9,6 g (29%) of the compound of formula (101) are obtained, m.p. 65–69° C.

Example A4

Preparation of 1-(1-cyano-cyclohexyloxy)-2-(1-cyano-cyclohexyl)-2,4,4-tetra-methyl-pyrrolidin (106)

7.65 g ( 0.06 Mol) 2,4,4-trimethyl-pyrrolin-1-oxid [prepared according to M. J. Turner et al.: Synth. Commun. 16 (11),1377 (1986)] and 22 g (0.09 Mol) azobis-(1-cyanocyclohexan) are dissolved in 75 ml chlorbenzene. After careful purge with argon the solution is heated to 100° C. for 8,5 hours under argon atmosphere. Chlorbenzene is distilled off on the rotary evaporator. The residue subjected to column chromatography on silica gel (hexane/ethylacetate 9:1) and recrystallyzed from dichlormethane/hexane. 10,1 g (49%) of the compound of formula (102) are obtained, m.p. 124°–127° C.

TABLE 2

| Nr. | Compound | m.p. (° C.) | C(%), H(%), N(%) Ber./Gef. |
|---|---|---|---|
| 105 | | 65–69 | 68.40 9.57 15.95<br>68.34 9.47 15.91 |
| 106 | | 124–127 | 73.43 9.68 12.23<br>73.27 9.26 12.23 |
| 107 | | | |

Compounds V-65 and V-70 (WACO) are commercially available.

B) Polymerizations using compounds of Table I and Table 2 as initiators

General remarks:

Solvents and monomers are distilled over a Vigreux column under argon atmosphere or under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for 30 minutes, weighing the remaining polymer and subtract the weight of the initiator.

Characterization of the polymers is carried out by MALDI-MS (Matrix Assisted Laser Desorption Ionization Mass Spectrometry) and/or GPC (Gel Permeation Chromatography).

MALDI-MS

Measurements are performed on a linear TOF (Time Of Flight) MALDI-MS LDI-1700 Linear Scientific Inc., Reno, USA. The matrix is 2,5-dihydroxybenzoic acid and the laser wavelength is 337 nm.

GPC

Is performed using RHEOS 4000 of FLUX INSTRUMENTS. Tetrahydrofurane (THF) is used as a solvent and is pumped at 1 ml/min. Two chromatography columns are put in series: type Plgel 5 μm mixed-C of POLYMER INSTRUMENTS, Shropshire, UK. Measurements are performed at 40° C. The columns are calibrated with low polydispersity polystyrenes having Mn from 200 to 2000000 Dalton. Detection is carried out using a RI-Detector ERC-7515A of ERCATECH AG at 30° C.

Example B1

Polymerization of n-butylacrylate using compound 101

In a 50 ml three neck flask, equipped with thermometer, cooler and magnetic stirrer, 654 mg ( 2.34 mmol) of compound 101 and 20 g ( 156 mmol) of n-butylacrylate are mixed and degased. The clear solution obtained is heated under argon to 120° C. Polymerization starts spontaneously and the temperature rises to 143° C. After 15 minutes, the exothermal reaction slowly stops and the viscosity of the solution increases. The reaction mixture is stirred for an additional 10 minutes at 145° C. and is then cooled to 80° C. The remaining monomer is removed by evaporation under high vacuum. 19.1 g (95%) of the initial monomer have reacted. A clear colourless viscous fluid is obtained.

MALDI-MS

Mn=3400, Mw=6100, PD=1.8

Example B2

Polymerization of n-butylacrylate using comround 102 in xylene

In a 100 ml three neck flask, equipped with thermometer, cooler and magnetic stirrer, 841 mg (2.34 mmol) of compound 102, 20 g (156 mmol) of n-butylacrylate and 10 g xylene are mixed and degased. The clear solution obtained is heated under argon to 130° C. Polymerization starts spontaneously and the temperature rises to 141° C. After 10 minutes, the exothermal reaction slowly stops. The reaction mixture is then cooled to room temperature. The remaining monomer and solvent is removed by evaporation at 80° C. under high vacuum. 18.1 g (87%) of the initial monomer have reacted. A clear colourless viscous fluid is obtained.

GPC

Mn=7400, Mw=14800, PD=2

Example B3

Polymerization of n-butylacrylate using compound 101 in octane

In a 50 ml three neck flask, equipped with thermometer, cooler and magnetic stirrer, 279 mg (1.75 mmol) of compound 101 and 15 g ( 117 mmol) of n-butylacrylate in 7,5g octane are mixed and degased. The clear solution obtained is heated under argon to 130° C. Polymerization starts spontaneously. After 15 minutes, the exothermal reaction slowly stops and the viscosity of the solution increases. The reaction mixture is stirred for an additional 2.5 h at 130° C. and is then cooled to 80° C. The remaining monomer is removed by evaporation under high vacuum. 14.0 g (93%) of the initial monomer have reacted. A clear colorless viscous fluid is obtained.

GPC analysis: Mn 8500, Mw: 15300, Polydispersity (PD): 1.8

Example B4

Polymerization of n-butylacrylate using compound 102 in toluene 631 mg (1.8 mmol) of compound 102, 15 g (117 mmol) n-butylacrylat and 7.5 g toluene are reacted at 110° C. for 2.5 h. After evaporation of volatile components 14.8 g (95%) polymer are obtained.

GPC

Mn=7100, Mw=13200, PD=1.8

Example B5

Polymerization of n-butylacrylate using compound 102 in heptane 1.4 g (3.9 mmol) of compound 102, 5 g (39 mmol) n-butylacrylate and 2.5 g heptane are reacted at 100° C. for 22 h. After evaporation of volatile components 5.9 g (91%) of viscous liquid are obtained.

GPC

Mn=1300, Mw=2100, PD=1.6

Example B6

Polymerization of methylmethacrylate (MMA) using compound 102 in toluene 808 mg (2.25 mmol) of compound 102, 15 g (150 mmol) MMA and 7.5 g toluene are reacted at 110° C. for 2.5 h. After evaporation of volatile components 9.2 g (61%) of a solid white foam are obtained.

GPC

Mn=3000, Mw=5800, PD=1.9

Example B7

Polymerization of methacrylic acid -2-diamino-ethylester (MADMAEE) using compound 102 in heptane 686 mg (1.91 mmol) of compound 102, 20 g (127 mmol) MADMAEE and 10 g heptane are reacted at 100° C. for 5 h. After evaporation of volatile components 13.1 g (66%) of a partially solid material are obtained.

GPC

Mn=4300, Mw=7400, PD=1.7

Example B8

Polymerization of methacryic acid-glycidylester (MAGE) using compound 102 in dioxane 1.52 g (4.22 mmol) of compound 102, 20 g (141 mmol) MAGE and 10 g dioxane are reacted at 100° C. for 1 h. After evaporation of volatile components 13.9 g (62%) of a viscous material are obtained.

GPC

Mn=3800, Mw=6100, PD=1.6

Example B9

Polymerization of acrylic acid-4-hvdroxybutylester using comgound 102 in dioxane 1.66 g (4.6 mmol) of compound 102, 22.2 g (154 mmol) of acrylic acid-4-hydroxybutylester and 11.1 g dioxane are reacted at 105° C. for 2.5 h. After evaporation of volatile components 20.1 g (83%) of a viscous material are obtained.
GPC
Mn=4000, Mw=7100, PD=1.8

Example B10
Polymerization of acrylic acid-(3-sulfopropylester) Kaliumsalt using compound 102

0.232 g (0.65mmol) of compound 102, 10 g (43 mmol) acrylic acid-(3-sulfopropylester) Kalium-salt, 90 g ethylenglykol and 10 g water are mixed, degassed and heated to 90° C. The mixture is reacted for 20 h. The clear polymer solution is poured into aceton. The white solid polymer is filtered off and dried under high vacuum. 5.8 g (56%) are obtained. $^1$H-NMR in $D_2O$ shows no acrylate double bond between 6–6.5 ppm, thus indicating that all monomer has reacted.

Example B11
Random copolymer from n-butylacrylate and methacrylic acid -2-diamino ethylester (MADMAEE) using compound 102

1.37 g (3.81 mmol) of compound 102, 16.3 g (127 mmol) of n-butylacrylate, 20 g (127 mmol) of MADMAEE and 18 g octane are reacted at 130° C. for 2.5 h. After evaporation of volatile components 30.7 g (85%) copolymer are obtained.
GPC
Mn=5300, Mw=9200, PD=1.7

Example B12
Random copolymer from n-butylacrylate and methylmethacrylate using compound 102

2.17 g (6.03 mmol) of compound 102, 7 g (70.3 mmol) methylmethacrylate and 10 g (70.3 mmol) of n-butylacrylate in 8.5 g dioxane are degassed and reacted at 105° C. for 5 h under argon. After evaporation of volatile components 15 g (75%) copolymer are obtained.
GPC
Mn=2200, Mw=3800, PD=1.7

Example B13
Blockcopolymer from n-butylacrylate and acrylic acid-2-ethoxyethylester 3 g (8.34 mmol) of compound 102, 17.8 g (139 mmol) n-butylacrylate and 9 g toluene are reacted at 115° C. for 2,5 h. After evaporation of volatile components 13.9 g (61%) polymer are obtained. 20 g (139 mmol) acrylic acid-2-ethoxyethylester and 19 g toluene are added. The mixture is reacted at 115° C. for 2,5 h. After evaporation of volatile components 33.4 g (98%, based on the second monomer) copolymer are obtained. Total conversion is 60%.
GPC
Mn=3900, Mw=7800, PD=2

Example B14
Blockcogolymer from n-butylacrylate and acrylic acid-3-hydroxypropylester 3 g (8.34 mmol) of compound 102, 17.8 g (139 mmol) n-butylacrylate and 9 g dioxane are reacted at 105° C. for 2,5 h. After evaporation of volatile components 15.2 g (69%) polymer are obtained. 18.1 g (139 mmol) acrylic acid-3-hydroxypropylester and 18 g dioxane are added. The mixture is reacted at 105° C. for 2 h. After evaporation of volatile components 33.8 g (100%, based on the second monomer) copolymer are obtained. Total conversion is 69%.

GPC
Mn=3300, Mw=11500, PD=3.5

Example B15
Blockcopolymer from n-butylacrylate and acrylic acid 1.85 g (5.1 mmol) of compound 102, 20 g (156 mmol) n-butylacrylate and 10 g octane are reacted at 130° C. for 2,5 h. After evaporation of volatile components 21.3 g (97%) polymer are obtained. 1.12 g (15.6 mmol) acrylic acid and 11 g dioxane are added. The mixture is reacted at 105° C. for 2.5 h. After evaporation of volatile components 22.3 g (89%, based on the second monomer) copolymer are obtained.
GPC
Mn=4200, Mw=6500, PD=1.6

Example B16
Blockcopolymer from n-butylacrylate and methylmethacrylate 3.08 g (8.58 mmol) of compound 102, 20 g (156 mmol) n-butylacrylate and 10 g octane are reacted at 130° C. for 2,5 h. After evaporation of volatile components 22.7 g (98%) polymer are obtained. 15.6 g (156 mmol) methylmethacrylate and 10 g octane are added. The mixture is reacted at 130° C. for 2.5 h. After evaporation of volatile components 29.4 g copolymer are obtained. Total conversion is 43%.
GPC
Mn=2600, Mw=3900, PD=1.5

Example B17
Blockcopolymer from n-butylacrylate and methacrylic acid-2-dimethylamino-ethylester/(MADMAEE)

1.37 g (3.81 mmol) 102, 16.3 g (127 mmol) n-butylacrylate and 18 g octane are reacted at 130° C. for 2.5 h. Volatile components are evaporated and 20 g (127 mmol) MADMAEE in 18 g octane are added and reacted at 130° C. for 2.5 h. After evaporation of volatile components 30.3 g (80%) of blockcopolymer are obtained.
GPC
Mn=4800, Mw=9700, PD=2

Example B18
Homololymerization of styrene using compound 102

In a 50 ml flask 0.719 g (2 mmol) of compound 102, 20.9 g (200 mmol) styrene and 20 g toluene are mixed. The mixture is refluxed and polymerized for 6 h. After evaporation of volatile components 9.73 g (47 %) polymer are obtained.
GPC
Mn=3100, Mw=4900, PD=1.6

Example B19
In situ preparation of initiator from compound 104 and azobisisobutyronitrile and simultaneous polymerization of n-butylacrylate 0.447 g (3.12 mmol) 104, 0.512 (3.12 mmol) azobisisobutyronitrile (AIBN), 20 g (156 mmol) n-butylacrylate and 10 g octane are mixed in a 100 ml flask and degassed. The mixture is reacted at 80° C. for 2 h under stirring. Temperature is slowly raised to 130° C. Polymerization is conducted at 130° C. for 2.5 h. After evaporation of volatile components 5.1 g (21%) polymer are obtained.
GPC
Mn=1200, Mw=1700, PD=1.4

Example B20
In situ preparation of initiator from compound 104 and V-65 with simultaneous polymerization of n-butylacrylate 0.670 g (4.7 mmol) of compound 104, 1.162 g (4.7 mmol) of compound V-65, 30 g (234 mmol) n-butylacrylate and 15 9 octane are mixed in a 100 ml flask and degased. The mixture is stirred for 30 min. at 800° C. The temperature is slowly raised to 130° C. The mixture is polymerized at 130° C. for 2.5 h. After evaporation of volatile components 11.4 g polymer are obtained, corresponding to 38% conversion.

GPC

Mn=2800, Mw=5700, PD=2.0

Example B21

In situ preparation of initiator from compound 104 and V-65 with subsequent polymerization of n-butylacrylate 0.670g (4.7 mmol) of compound 104, 2.034 g (8.2 mmol) of compound V-65 and 15 g octane are mixed in a 100 ml flask and degased. The mixture is stirred for 1.25 h at 80° C. 30 g (234 mmol) of n-butylacrylate are added and the temperature is slowly raised to 130° C. The mixture is polymerized at this temperature for 3 h. After evaporation of volatile components 80% conversion are obtained.

GPC

Mn=6200, Mw=12200, PD=1.97

Example B22

Polymerization of n-butylacrylate using compound 105

In a 50 ml three neck flask, equipped with thermometer, cooler and magnetic stirrer, 1643 mg (6,24 mmol) of compound 101 and 20 g (156 mmol) of n-butylacrylate are mixed and degased. The clear solution obtained is heated under argon to 115° C. Polymerization starts spontaneously and the temperature rises to 130° C. After 15 minutes, the exothermal reaction slowly stops and the viscosity of the solution increases. The reaction mixture is stirred for an additional 15 minutes at 145° C. and is then cooled to 80° C. The remaining monomer is removed by evaporation under high vacuum. 19,3 g (97%) of the initial monomer have reacted. A clear colourless viscous fluid is obtained.

MALDI-MS

Mn=3000, Mw=5300, PD=1,7

GPC

Mn=3100, Mw=5400, PD=1,7

Example B23

Polymerization of n-butylacrylate using compound 106

In a 50 ml three neck flask, equipped with thermometer, cooler and magnetic stirrer, 804 mg (2,34 mmol) of compound 102 and 20 g (156 mmol) of n-butylacrylate are mixed and degased. The clear solution obtained is heated under argon to 145° C. Polymerization starts spontaneously and the temperature rises to 170° C. After 15 minutes, the exothermal reaction slowly stops and the viscosity of the solution increases. The reaction mixture is stirred for an additional 15 minutes at 145° C. and is then cooled to 80° C. The remaining monomer is removed by evaporation under high vacuum. 19,5 g (98%) of the initial monomer have reacted. A clear colourless viscous fluid is obtained.

MALDI-MS

Mn=4600, Mw=7300, PD=1,6

Example B24

Polymerization of n-butylacrylate using compound 106

1608 mg ( 4.68 mmol) of compound 106 and 20 g (156 mmol) n-butylacrylate in 10 ml n-octane are reacted at 130° C. for 2.5 h. After evaporation of volatile components 17.1 9 (79%) polymer are obtained.

GPC

Mn=3400, Mw=5700, PD=1.7

Example B25

Polymerization of acrylic acid-2-ethoxyethylester using compound 105

1.96 g (4.16 mmol) of compound 105, 20 g (139 mmol) acrylic acid-2-ethoxyethylester in 10 g toluene are polymerized in a 50 ml flask at 115° C. for 5 h. After evaporation of volatile components 17.4 9 (87%) of a viscous polymer are obtained.

GPC

Mn=3900, Mw=7600, PD=1.9

Example B26

Polymerization of methacrylic acid-2-dimethylaminoethylester using compound 106

1.309 g (3.81 mmol) of compound 106, 20 g (127 mmol) methacrylic acid-2-dimethylaminoethylester and 10 g octane are reacted at 130° C. for 2.5 h. After evaporation of volatile components 18.4 g (92%) of a viscous to solid polymer is obtained.

GPC

Mn=4100, Mw=8300, PD=2

Example B27

Blockcopolymerization of n-butylacrylate and methacrylic acid-2-dimethylamino-ethylester using compound 106

2.411 g (7.02 mmol) of compound 106 and 20 g (156 mmol) n-butylacrylate, dissolved in 10 g n-octane, are reacted at 130° C. for 2.5 h. Volatile components are evaporated under vacuum at 80° C. and the residue is isolated. Conversion is 93%. In a second step 12.3 g (78 mmol) methacrylic acid-2-dimethylaminoethylester and 16 g n-octane are added and at 130° C. for 2.5 h polymerized. After evaporation of volatile components 29.8 g (92%) copolymer are obtained.

GPC

Mn=4200, Mw=8600, PD=2

Example B28

Blockcopolymerization of n-butylacrylate and iso-butylacrylate using compound 105

1.233 g (4.68 mmol) of compound 105 and 20 g (156 mmol) n-butylacrylate are reacted at 130° C. for 40 min. The reaction mixture is cooled down to 100° C. and 20 g (156 mmol) iso-butylacrylate are added. Reaction is continued at 130° C. for 1.5 h. After evaporation of volatile components 34.7 g (87%) copolymer are obtained.

GPC

Mn=6200, Mw=11600, PD=1.8

Example B29

Random copolymer of n-butylacrylate and methacrylic acid-2-dimethylaminoethylester usinq compound 106

2.617 g (7.62 mmol) of compound 106, 16.3 g (127 mmol) n-butylacrylaet, 20 g (127 mmol) methacrylic acid-2-dimethylaminoethylester and 18 g octane are reacted at 130° C. for 2,5 h. After evaporation of volatile components 36.4 g (93%) of a viscous liquid are obtained.

GPC

Mn=3800, Mw=5800, PD=1.5

Example B30

Block-copolymer of n-butylacrylat and methacrylic acid-2-dimethylaminoethylester (MADMAEE) using compound 106

2,617 g (7.62 mmol) of compound 106 in 8.2 g octane and 16.3 g (127 mmol) n-butylacrylate are polymerized at 130° C. for 2.5 h. After evaporation of volatile components 17.8 g (93%) of the first polymer block are obtained. 18 g octane and 20 g (127 mmol) MADMAEE are subsequently polymerized at 130° C. for 2.5 h. After evaporation of volatile components 36.3 g (93%) of the block-copolymer are obtained.

GPC

Mn=3300, Mw=11300, PD=3.4

Example B31

Random copolymer of n-butylacrylate and acrylic acid using compound 105

1.3 g (4.93 mmol) of compound 105, 18.9 g (147.8 mmol) n-butylacrylate, 1.18 g (16.4 mmol) acrylic acid in 10 g octane are reacted at 130° C. for 2.5 h. After evaporation of volatile components 20.7 g (97%) of a clear viscous liquid are obtained.

GPC
  Mn=3800, Mw=8200, PD=2.2
Example B32
Triblock-copolymer of n-butylacrylate/methacrylic acid-2-dimethylaminoethylester/n-butylacrylate using compound 106

3.617 g (10.53 mmol) of compound 106, 7.5 g (58.5 mmol) n-butylacrylate, 9.2 g (58.5 mmol) MADMAEE and again 7.5 g (58.5 mmol) n-butylacrylate in octane are polymerized successively according to example B30 at a temperature of 130° C. for 2.5 h for each step. Conversions for each step are 91%, 95% and 34%.
GPC
  Mn=2600, Mw=4400, PD=1.7
Example 33
Homopolymerization of styrene 0.679 g (2 mmol) of compound 106, 20.9 g (200 mmol) styrene and 20 g toluene are refluxed for 6 h. After evaporation of volatile components 19.6 g (94%) polymer are obtained.
GPC
  Mn=9000, Mw=10800, PD=1.2
Example B34
Homopolymerization of styrene 0.527 g (2 mmol) of compound 105, 20.9 g (200 mmol) styrene and 20 g toluene are refluxed for 6 h. After evaporation of volatile components 19.6 g (94%) polymer are obtained.
GPC
  Mn=9400, Mw=11400, PD=1.2
Example B35
Pseudo-block-copolymerisation of polystyrene of example B34 with styrene 5 g of the polymer of example 34 are mixed with 5 g styrene and 20 g toluene. The solution is degased and reacted at 110° C. for 6 h. After evaporation of volatile components 7.7 g (54%) polymer are obtained.
GPC
  Mn=13500, Mw=17500, PD=1.3
Example B36
Block-copolymer of styrene and n-butylacrylate 62.5 g (0.6 mol) styrene are polymerized with 1.68 g (6 mmol) of compound 105 in 40 g octane at 110° C. for 6 h. 42 g (66%) of polystyrene are obtained.
GPC
  Mn=9400, Mw=11400, PD=1.2

To 30 9 of the polystyrene 40 g (312 mmol) n-butylacrylate and 40 g octan are added. The mixture is heated to 130° C. for 6 h under stirring. n-butylacrylate is reacted to 98% and 69 g of the block copolymer are obtained.
GPC
  Mn=13500, Mw=19100, PD=1.4
Example B37
In situ preparation of initiator from compound 107 and azobisisobutyronitrile with simultaneous polymerization of n-butylacrylate In a 100 ml flask 0.397 g (3.12 mmol) of compound 107, 0.512 g (3.12 mmol) AIBN, 20 g (156 mmol) n-butylacrylate and 10 g octane are mixed. The mixture is stirred at 80° C. for 2 h. The temperature is slowly raised to 130° C. and the mixture is reacted for 2.5 h at this temperature. After evaporation of volatile components 17.5 g (83%) of a viscous liquid are obtained.

GPC
  Mn=6500, Mw=13200, PD=2
Example B38
In situ preparation of initiator from compound 107 and V-65 with simultaneous polymerization of n-butylacrylate In a 100 ml flask 0.397 g (3.12 mmol) of compound 107, 0.775 g (3.12 mmol) of compound V-65, 20 g (156 mmol) n-butylacrylate and 10 g octane are mixed. The mixture is stirred for 30 min. at 80° C. Temperature is raised slowly to 130° C. and the mixture is reacted for 2.5 h. After evaporation of volatile components 65% conversion is obtained.
GPC
  Mn=5400, Mw=9200, PD=1.7
Example B39
In situ preparation of initiator from compound 107 and V-65 with subsequent polymerization of n-butylacrylate In a 100 ml flask 0.595 g (4.7 mmol) of compound 107, 2.034 g (8.2 mmol) of compound V-65 and 15 g octane are mixed. The mixture is stirred at 80° C. for 1.25 h. 30 g (234 mmol) n-butylacrylate are added and the temperature is slowly raised to 130° C. The mixture is allowed to react for 5 h at this temperature. After evaporation of volatile components 20% conversion is achieved.
GPC
  Mn=5800, Mw=9000, PD=1.66
Example B40
In situ preparation of initiator from compound 107 and V-70 with simultaneous polymerization of n-butylacrylate In a 100 ml flask 0.595 g (4.7 mmol) of compound 107, 2.526 g (8.2 mmol) of compound V-70, 30 g (234 mmol) n-butylacrylate and 15 g octane are mixed. The mixture is stirred for 15 min. at 60° C. Temperature is raised slowly to 130° C. and the mixture is reacted for 5 h. After evaporation of volatile components 66% conversion is obtained.
GPC
  Mn=4400, Mw=7600, PD=1.73
Example B41
In situ preparation of initiator from compound 107 and V-70 with subsequent polymerization of n-butylacrylate In a 100 ml flask 0.595 g (4.7 mmol) of compound 107, 2.526 g (8.2 mmol) of compound V-70 and 15 g octane are mixed. The mixture is stirred at 60° C. for 1.25 h. 30 g (234 mmol) n-butylacrylate are added and the temperature is slowly raised to 130° C. The mixture is allowed to react for 5 h at this temperature. After evaporation of volatile components 20% conversion is achieved.
GPC: Mn=5500, Mw=9400, PD=1.72

What is claimed is:

1. A compound of formula (I)

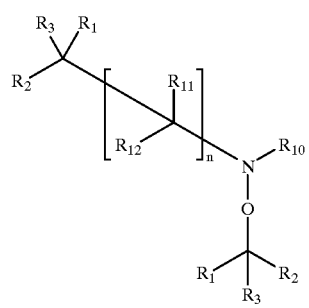

wherein n is 0 or 1;

$R_1$, $R_2$, $R_3$ are each independently of one another $NO_2$, cyano, —C(O)—$R_7$, —$OR_8$, unsubstituted $C_1$-$C_{12}$alkyl or phenyl, which is unsubstituted or substituted by $C_1$–$C_4$alkyl, $C_1$–$C_4$alkoxy, cyano, hydroxy, carboxy, $C_1$–$C_4$alkylamino or di($C_1$–$C_4$alkyl)amino;

or $R_2$ and $R_3$, together with the linking carbon atom, form a $C_5$–$C_7$ cycloalkyl radical;

$R_7$ is, $C_1$–$C_8$alkyl or phenyl;

$R_8$ is $C_1$–$C_8$alkyl or $C_2$–$C_8$alkyl which is substituted by at least one hydroxy group and $R_{10}$ is $C_4$–$C_{18}$alkyl bound via a tertiary C-atom to the nitrogen atom, phenyl or $C_9$–$C_{11}$phenylalkyl;

if n is 1

$R_{11}$ is $C_1$–$C_{18}$alkyl, $C_7$–$C_9$phenylalkyl or $C_3$–$C_{12}$cycloalkyl or $R_{10}$ and $R_{11}$ together form a $C_2$–$C_6$alkylene bridge which is unsubstituted or substituted with $C_1$–$C_4$alkyl;

$R_{12}$ is, unsubstituted $C_1$–$C_4$alkyl or phenyl.

2. A compound according to claim 1, wherein n is 0

$R_1$ is cyano;

$R_2$ and $R_3$ are each independently of one another unsubstituted $C_1$–$C_{12}$alkyl or phenyl;

or $R_2$ and $R_3$, together with the linking carbon atom, form a $C_5$–$C_7$ cycloalkyl radical;

$R_{10}$ is $C_4$–$C_{12}$alkyl bound via a tertiary C-atom to the nitrogen atom, $C_9$–$C_{11}$,phenylalkyl or phenyl.

3. A compound according to claim 1, wherein n is 1

$R_1$ is cyano;

$R_2$ and $R_3$ are each independently of one another unsubstituted $C_1$–$C_{12}$alkyl or phenyl;

or $R_2$ and $R_3$, together with the linking carbon atom, form a $C_5$–$C_7$cycloalkyl radical;

$R_{10}$ is $C_4$–$C_{12}$alkyl bound via a tertiary C-atom to the nitrogen atom, $C_9$–$C_{11}$phenylalkyl or phenyl; or $R_{10}$ and $R_{11}$ together form a $C_2$–$C_6$alkylene bridge which is unsubstituted or substituted with $C_1$–$C_4$alkyl; and $R_{12}$ is $C_1$–$C_4$alkyl.

4. A compound of formula (I) according to claim 1, which is a) N-(1,1,3,3,-tetramethyl-butyl)-N,O-bis-(1-cyano-1-methyl-ethyl)-hydroxylamine, b) N-(1,1,3,3,-tetramethyl-butyl)-N,O-bis-(1-cyano-cyclohexyl)-hydroxylamine, c) 1-(1-cyano-1methyl-ethoxy)-2-(1-cyano-1-methyl-ethyl)-2,5,5-tetra-methyl-pyrrolidine or d) 1-(1-cyano-cyclohexyloxy)-2-(1-cyano-cyclohexyl)-2,4,4-tetra-methyl,pyrrolidine.

* * * * *